(12) United States Patent
Tochon et al.

(10) Patent No.: US 8,104,531 B2
(45) Date of Patent: Jan. 31, 2012

(54) STACKED PLATE HEAT EXCHANGER INCLUDING A DEVICE FOR EVALUATING THE EXTENT TO WHICH IT HAS BECOME COATED IN SCALE

(75) Inventors: Patrice Tochon, Uriage (FR); Patrice Clement, Saint Egreve (FR); Bruno Ladevie, Marssac sur Tarn (FR)

(73) Assignee: Commissariat a l'Energie Atomique, Paris (FR)

( * ) Notice: Subject to any disclaimer, the term of this patent is extended or adjusted under 35 U.S.C. 154(b) by 544 days.

(21) Appl. No.: 12/176,434

(22) Filed: Jul. 21, 2008

(65) Prior Publication Data

US 2009/0000764 A1    Jan. 1, 2009

Related U.S. Application Data

(63) Continuation of application No. PCT/FR2007/050705, filed on Jan. 29, 2007.

(30) Foreign Application Priority Data

Feb. 28, 2006  (FR) ...................................... 06 50697

(51) Int. Cl.
*B60H 1/00* (2006.01)
*F28D 7/02* (2006.01)
*F28F 3/00* (2006.01)

(52) U.S. Cl. .................... 165/11.1; 165/165; 165/166

(58) Field of Classification Search ................. 165/11.1, 165/165, 166
See application file for complete search history.

(56) References Cited

U.S. PATENT DOCUMENTS

| | | | | |
|---|---|---|---|---|
| 5,590,706 | A | * | 1/1997 | Tsou et al. .................... 165/11.1 |
| 5,992,505 | A | * | 11/1999 | Moon ........................... 165/11.1 |
| 6,386,272 | B1 | | 5/2002 | Starner et al. |
| 6,499,876 | B1 | | 12/2002 | Baginksi et al. |
| 6,834,515 | B2 | | 12/2004 | Sunder et al. |

FOREIGN PATENT DOCUMENTS

EP             1 398 593 A2    3/2004

* cited by examiner

*Primary Examiner* — Ljiljana Ciric
(74) *Attorney, Agent, or Firm* — Burr & Brown

(57) ABSTRACT

A plate-type heat exchanger including a plurality of stacked plates and a device for evaluating the extent to which the fluid circuit(s) have become coated in scale, whereby the evaluating device has an electrical resistor which is thermally connected to a plate located at the end of the stack while measuring the temperature in the immediate vicinity of the resistor.

9 Claims, 2 Drawing Sheets

STACKED PLATE HEAT EXCHANGER INCLUDING A DEVICE FOR EVALUATING THE EXTENT TO WHICH IT HAS BECOME COATED IN SCALE

FIELD OF THE INVENTION

The invention relates to the field of heat exchangers and, more especially, plate-type heat exchangers. More specifically, it relates to plate-type heat exchangers fitted with devices for evaluating the extent to which the fluid circuits between its plates have become coated in scale (fouled). It refers more especially to a design of a device for evaluating the extent of coating in scale which outputs a reliable signal regardless of the type of heat exchange (liquid-gas or liquid-liquid) which occurs inside the heat exchanger and which can also be adapted to various types of plate-type heat exchangers, especially existing heat exchangers.

BACKGROUND OF THE INVENTION

Generally speaking, the problem of heat exchangers becoming coated in scale is of major importance insofar as it has an important impact on the design and operation of plant which includes this type of heat exchanger. This coating in scale is caused by the deposition of solid materials which flow through the heat exchanger and are then deposited in those areas where the velocity of the fluid is slower.

Thus, in the chemical and petrochemical industries as well as in the generation of energy by thermal or nuclear means, fouling in heat exchangers has a direct impact on their performance and hence on generation efficiency. Not only this, the fouling observed in certain types of plants increases the potential risk of overheating under certain conditions and makes it necessary to reduce production in order to maintain adequate safety margins.

In addition, in the agri-foodstuff industry in particular, fouling of heat exchangers is also crucial in as much as it has measurable consequences in terms of health and safety. This is why heat exchangers have to undergo frequent cleaning operations, the cost of which can be measured in terms of the time for which the means of production are idle and in terms of the consumption of detergent products.

Economic studies have demonstrated than the overall cost of fouling phenomena is especially high and that this prevents the entry of plate-type heat exchangers into certain markets where fouling phenomena have to be well controlled.

Attempted improvements have already been suggested in order to reduce fouling of plate-type heat exchangers; these consist in designing the geometry of the heat exchange areas in a specific manner. The physical phenomena which cause fouling are still not fully understood and no really satisfactory solution has yet been proposed in order to control such fouling. Consequently, on an industrial scale, fouling of heat exchangers is managed empirically and cleaning cycles are scheduled on the basis of knowledge acquired through experience. It is apparent that such a technique is not really suitable for using heat exchangers which employ fluids which have varying compositions. Furthermore, when a cleaning intervention is undertaken too late, fouling may be bad enough to involve extensive, tricky operations. Consequently, cleaning interventions are often scheduled more frequently than necessary and this has a negative impact on the plant's production time.

There is therefore a palpable need to measure or at least evaluate the degree of fouling using a method which can be performed in real-time.

Devices for evaluating the fouling of heat exchangers have already been fitted on gas-liquid tubular heat exchangers. Solutions like those described, in particular, in Document U.S. Pat. No. 6,386,272 are based on the principle of heat flow meters, i.e. on measuring temperature differences either side of a wall. Unfortunately, this principle which works for gas-liquid tubular heat exchangers cannot be transferred to plate-type heat exchangers. Temperature measurements using the heat flow meter principle require a thick wall between the two temperature measuring points and this is virtually incompatible with the plate thickness usually used in heat exchangers which are of the order of 0.5 nm approximately. Moreover, the heat flow meter principle is less sensitive in the context of liquid-liquid heat exchange which is, however, the most commonly-encountered type of heat transfer in the case of plate-type heat exchangers.

One object of the invention is therefore to provide a plate-type heat exchanger which has a device for evaluating the extent to which it has become coated in scale and which works regardless of the type of heat transfer used by the heat exchanger (gas-liquid, gas-gas or liquid-liquid)

Another object of the invention is to provide a solution which can be simply adapted to all types of plate-type heat exchangers, whether they are of a new design or with a view to fitting it in existing heat exchangers.

SUMMARY OF THE INVENTION

The invention therefore relates to a plate-type heat exchanger which comprises, in a known manner, a plurality of stacked plates which define, between them, various fluid circuits which are involved in heat exchange. In a known manner, this heat exchanger includes a device for evaluating the extent to which it has become coated in scale (fouled).

According to the invention, the device for evaluating the extent of fouling comprises an electrical resistor which is thermally connected to the plate located at the end of the stack. The evaluation device also comprises means of measuring the temperature in the immediate vicinity of said electrical resistor.

In other words, the invention involves installing, inside the heat exchanger in a peripheral area, an electrical resistor which makes it possible to amplify the heat flow which is naturally transported inside the heat exchanger by dissipating a determined quantity of heat at a desired instant. This way, changes in temperature over time close to the resistor as a function of the quantity of heat which the latter releases are directly proportional to the extent to which the plate, with which the resistor is in contact, has become coated in scale. In fact, the extent of fouling of the fluid circuit modifies the specific heat of the plate and thus the rate at which its temperature can rise. Such a solution has many advantages because the temperature increase is the result of a quantity of energy which is externally introduced at a level which is higher than the heat flow resulting from the heat exchange phenomena for which the heat exchanger is designed. Detection is therefore highly sensitive and virtually insensitive to the heat exchange phenomena which occur in the heat exchanger.

A second important advantage is the fact that the electrical resistor and the temperature measuring device are located at the end of the heat exchanger. In fact, research has demonstrated that fouling of a heat exchanger is uniform over all the plates of the circuit, including the edge plates. Evaluating the overall fouling of a heat exchanger by making a measurement on an end plate in the stack is therefore representative. The resulting advantage is the fact that the device for evaluating fouling can be fitted in a brand new heat exchanger or can be added to an existing heat exchanger by inserting the distinctive resistor. The presence of the device for evaluating fouling does not alter the performance of the heat exchanger or influence the friction losses of the fluid circuits in anyway whatsoever.

In practice, the electrical resistor can be placed between the plate located at the far end of the stack and the frame of the heat exchanger or, more generally, any component which forms a fixed or movable end for the stack of plates.

It is also possible to place the electrical resistor between the last plate in the stack and an additional plate which has the same geometry as the other plates but is not used in order to form the fluid circuits. This way, the electrical resistor comes into contact with the last plate in the stack which plays a role in defining the fluid circuits and is covered by an additional plate or "cosmetic" component which is pressed against the rest of the stack of plates.

Advantageously and in practice, this assembly may comprise a layer of insulating material located on the same side as the electrical resistor and opposite the end plate of the stack. In fact, in this case attempts are preferably made to minimize the heat exchanger' thermal losses into its surroundings so that the heat flow generated by the distinctive resistor is in the direction of the last plate of the heat exchanger which is involved in heat exchanges.

In practice, evaluating the extent to which the heat exchanger has become coated in scale involves supplying electrical energy to the electrical resistor periodically or in pulses or in timed stages so as to cause a local increase in the temperature of the plate which is fouled to a greater or lesser extent. Local measurement of the temperature makes it possible to compare changes in temperature in the vicinity of the distinctive resistor to predetermined change profiles. Depending on the departure from these reference profiles, it is possible to deduce any modification of the specific heat of the plate due to an additional thickness of coated scale.

Evaluating the extent of fouling of a heat exchanger in real-time can be used on a snapshot-basis in order to check the degree of fouling through the absolute or relative value of the thickness of coated scale or to provide a differential value which shows the fouling change dynamics. Statistics can be generated allowing follow-up of changes in these values.

In special cases where the heat exchanger is fitted with an automatic cleaning device, one can make provision for the device for evaluating the extent of fouling to output a signal which is used in order to control such cleaning devices in order to trigger them when fouling measurements so require and to switch them off when measurements indicate that the heat exchanger is in a satisfactory condition.

BRIEF DESCRIPTION OF THE DRAWINGS

In order that the way in which the invention is implemented and its resulting advantages may more readily be understood, the following description is given, reference being made to the accompanying drawings.

DETAILED DISCRIPTION OF THE INVENTION

As stated earlier, the invention relates to a plate-type heat exchanger equipped with a device making it possible, in real time, to evaluate the extent to which it has become coated in scale. Such a heat exchanger can be built in various ways, for example by using plates which are welded or brazed together and secured in a rigid frame or, as shown in FIG. 1, by using a set of plates which are stacked and tightened in a frame.

Figure 1:
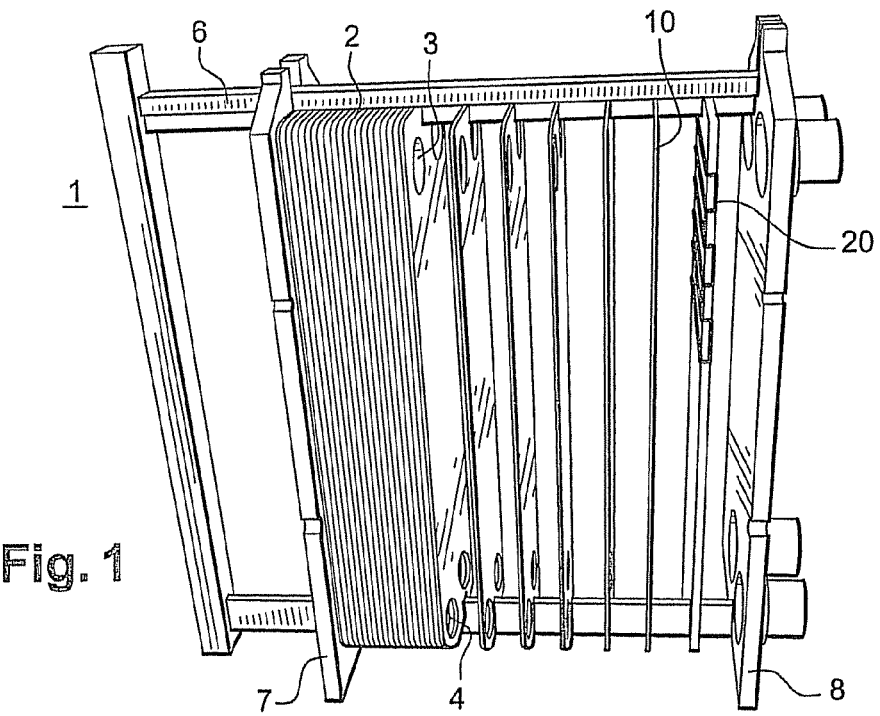
FIG. 1 is a schematic perspective view of a heat exchanger in accordance with the invention shown in a configuration obtained before tightening the various plates together.

More precisely, the heat exchanger (1) shown in FIG. 1 comprises a plurality of plates (2) stacked one against the other in order to define fluid circuits by means of openings (3, 4) through which fluids can pass. These plates are secured relative to each other by means of a frame (6) which includes two end elements (7, 8). End element (7) is movable and can be moved closer to end element (8) in order to press all the plates together. This heat exchanger (1) is therefore shown before tightening and this makes it possible to identify the last plate (10) of the heat exchanger which defines the fluid circuits. The heat exchanger also comprises the distinctive resistor mounted on element (20) located between last plate (10) and end element (8).

Figures 2, 3:
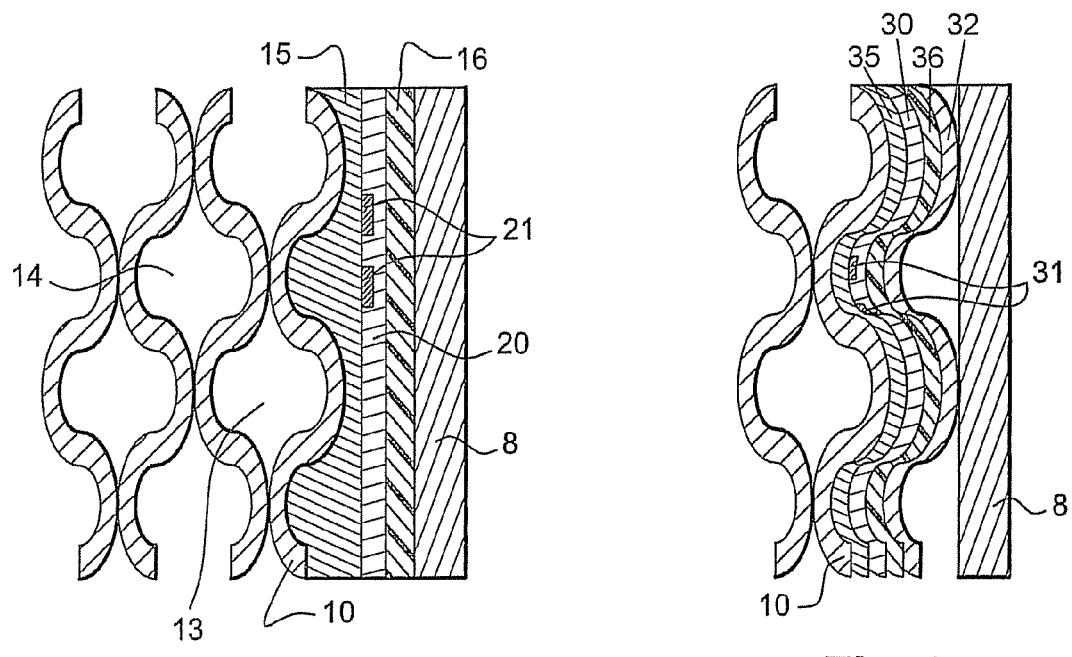
FIG. 2 is a schematic partial cross-sectional view of a first method of mounting the distinctive resistor between a plate and the heat exchanger's frame.
FIG. 3 is a schematic partial cross-sectional view of an alternative method of mounting the resistance between two plates having a similar geometry.

More precisely and as shown in FIG. 2, electrical resistor (21) can be mounted on a flat, flexible element (20) of the integrated-circuit type which is placed between end element (8) and last plate (10) which is involved in defining fluid circuits (13, 14) with interposed layers (15, 16) of insulating material (15, 16). Layer (15) which thermally connects resistor (21) to last plate (20) of the stack must have heat conduction properties which are substantially similar to those of plate (20), the thermal behaviour of which it must make possible to evaluate. In practice, this layer of insulating material (15) can typically be made of Kapton®.

The insulating layer (16) placed between element (20) which supports resistor (21) and end element (8) of the heat exchanger must be highly thermally insulating so that the heat flow generated by resistor (21) travels in the direction of plate (20) rather than towards the outside of the heat exchanger. In practice, this material is chosen depending on the performance of the heat exchanger and the other materials which are used to make plates (2, 10) and resistor support (20). The force applied to tighten the assembly of stacked plates to the two end elements makes it possible to ensure good heat conduction between electrical resistor (21) and plate (10), the scale coating of which is to be measured.

An alternative mounting system is shown in FIG. 3 whereby element (30) which supports electrical resistor (31) is placed between two plates having a similar geometry. Plate (10) which constitutes the last plate of the stack defining the fluid circuits is thermally connected to resistor (31) via a layer (35) which is similar to layer (15) in FIG. 2. An additional plate (32) which, typically, can be a plate which is identical to the other plates of the heat exchanger but not involved in defining the fluid circuits, sandwiches element (30) which supports resistor (31), also via an insulating layer (36). This insulating layer (36) is designed to direct the heat flow from the resistor towards the heat exchanger rather than towards the outside of the heat exchanger.

In practice, the distinctive resistor can be placed in various locations in the heat exchanger. As shown in FIG. 1, the resistor can be placed between the last plate and frame (8) but it can also be placed at the other end between the first plate and frame (7).

Figure 4:
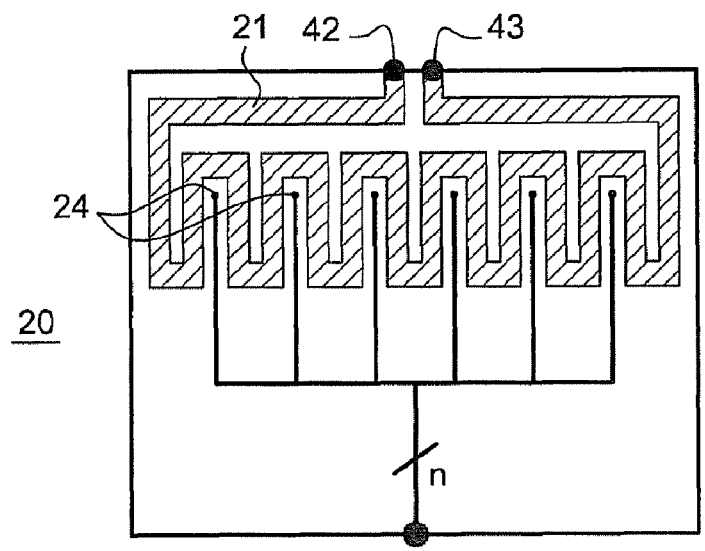
FIG. 4 is a top view of an element including the distinctive resistor.

In practice, the electrical resistor can be produced as shown in FIG. 4 as a metallic track deposited on a relatively flexible substrate. This resistor (21) is associated with one or more thermocouples (24) which are used to measure the temperature in the immediate vicinity of resistor (21). Two power supply terminals (42, 43) can be provided, together with all the necessary wiring and connectors, making it possible to supply the resistor from outside the heat exchanger. The resistor can also be produced as a one-piece component (20 and 21 are then a single object). In this case, the resistor extends over the full height but the measurement remains localized in the area of the thermocouples.

During operation, the sensor (20) consisting of resistor (21) and thermocouples (24) generates a heat flow when electric power is supplied to resistor (21). The resistor can be supplied by pulses or, preferably, by a current step. In this case, the resistor heats up and creates thermal non-equilibrium between the assembly consisting of the plates of the heat exchanger (10), insulating layer (15) and resistor (21) and its support (20). The thermocouples (24) placed close to electrical resistor (21) make it possible to record changes in temperature. In practice, it has been found that the higher the system's heat exchange capacity is, the more the response to this excitation is dampened.

Figure 5:
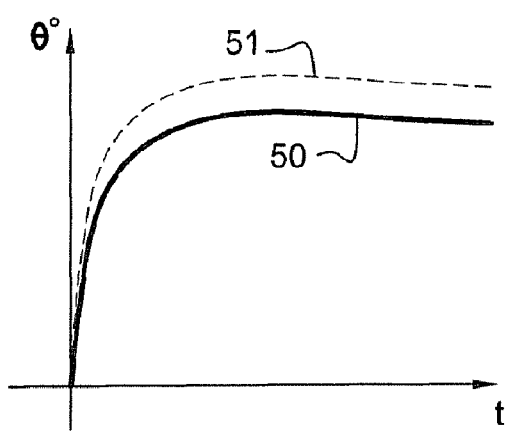
FIGS. 5 and 6 are graphs showing changes over time in the temperature measured in the vicinity of the distinctive resistor with variable heat exchange capacity and variable fouling respectively.

As shown in FIG. 5, if the system has a high heat exchange capacity, the temperature which is reached, shown by the solid line (50), is lower than the temperature reached if the heat exchange capacity is lower, shown by the dashed line (51). Given that the heat flow generated by resistor (21) is oriented almost exclusively inwards into the heat exchanger, the temperature change dynamics in the system depend only on the heat exchange capacity at the level of plate (10) of the heat exchanger and the thermal inertia of plate (10), this heat exchange capacity and this thermal inertia themselves being a function of the degree of fouling.

Figure 6:
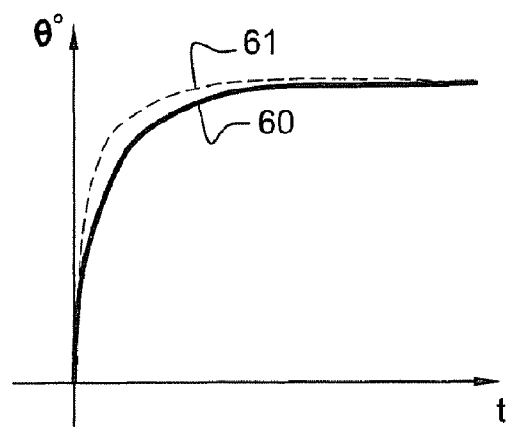

Calculations to determine the thermal behaviour of such systems can be directly modelled on the thermal-dipole method (Maillet, D., Degiovanni, *Méthode analytique de conduction inverse appliquée à la mesure du coefficient de transfert local sur un cylindre en convection forcée*, [Reverse heat-conduction analytical method applied to measuring the local transfer coefficient on a cylinder with forced convection], *Revue de physique appliqué*, Volume 24, pages 741-759, 1989). Thus, by analysing the sensitivity to these parameters, it can be demonstrated that, firstly, the system is sensitive and, secondly, that the effects of specific-heat modification are uncorrelated due to the thickness of the extra coating of scale on the material of plate (10), which can be identified over short periods, and the heat exchange coefficient, which can be identified over longer periods. By performing these types of measurements periodically using pulses or steps, it is possible to obtain a network of curves which change over time, as illustrated in FIG. 6.

Thus, assuming the heat exchanger is operating under identical conditions, it is apparent that the change in temperature under conditions where fouling is slight, as shown by the solid line (60), is different to the change in the fouled condition, as shown by the dashed line (61). Analysing these changes therefore makes it possible, by prior calibration, to establish the relationship between temperature measurements and the average thickness of scale on the plate.

It is evident from the above that heat exchangers equipped with the device for evaluating the extent to which they have become coated in scale in accordance with the invention have numerous advantages. In fact, they:
- are sufficiently sensitive to output a representative signal, even in the case of heat exchangers where flows are relatively reduced,
- have the ability to be fitted in new heat exchangers or even be added to existing heat exchangers,
- have a relatively low cost because their operation is based on using a planar electrical resistor and a limited number of thermocouples.

The invention claimed is:

1. A stacked plate heat exchanger comprising a plurality of plates arranged in a stack and defining at least one fluid circuit and including an evaluation device for evaluating the extent to which the fluid circuit has become coated in scale, wherein no portion of the evaluation device is in direct contact with the fluid circuit and said evaluation device further comprising an electrical resistor which is thermally connected to a plate located at an end of the stack of plates and means for measuring the temperature in the immediate vicinity of said resistor.

2. The heat exchanger as claimed in claim 1, further comprising an end element that forms an outermost frame of the heat exchanger, wherein the electrical resistor is placed between the plate located at the end of the stack and the end element that forms an outermost frame of the heat exchanger.

3. The heat exchanger as claimed in claim 1, wherein the electrical resistor is placed between the plate located at the end of the stack and another plate within the stack.

4. The heat exchanger as claimed in claim 2, wherein the evaluation device further comprising a layer of an insulating material located between the electrical resistor and the outermost frame of the heat exchanger.

5. The heat exchanger as claimed in claim 1, wherein said evaluation device comprises a single electrical resistor.

6. A method for evaluating the extent to which a stacked plate heat exchanger has become coated in scale, said stacked plate heat exchanger including a plurality of plates arranged in a stack and defining at least one fluid circuit, said method comprising:
providing an evaluation device, wherein no portion of the evaluation device is in direct contact with the fluid circuit and wherein said evaluation device comprises an electrical resistor which is thermally connected to a plate located at the end of the plurality of plates and means for measuring the temperature in the vicinity of said resistor,
wherein said method involves supplying electric power to the electrical resistor, and then comparing changes in the temperature in the vicinity of said resistor to predetermined temperature change profiles.

7. The method as claimed in claim 6, wherein the electric power is supplied to the electrical resistor by periodic pulses.

8. The method as claimed in claim 6, wherein the electric power is supplied to the electrical resistor in current steps.

9. The method as claimed in claim 6, wherein the evaluation device outputs a signal which is used to control a device for cleaning the heat exchanger.

* * * * *

UNITED STATES PATENT AND TRADEMARK OFFICE
CERTIFICATE OF CORRECTION

PATENT NO. : 8,104,531 B2  
APPLICATION NO. : 12/176434  
DATED : January 31, 2012  
INVENTOR(S) : Patrice Tochon, Patrice Clement and Bruno Ladevie Page 1 of 1

It is certified that error appears in the above-identified patent and that said Letters Patent is hereby corrected as shown below:

Title Page, Item (73), Assignee: *please add* --Armines, Paris (FR)--

Signed and Sealed this
Seventeenth Day of April, 2012

David J. Kappos
*Director of the United States Patent and Trademark Office*